United States Patent [19]

Martin, Jr. et al.

[11] 3,987,361

[45] Oct. 19, 1976

[54] NUCLEAR MAGNETIC RESONANCE TEMPERATURE EQUILIBRATION AND METHOD FOR OIL IN WAX DETERMINATION

[75] Inventors: James M. Martin, Jr.; Roy C. Heaton, both of Pasadena; Richard H. Coe, Seabrook, all of Tex.

[73] Assignee: Shell Oil Company, Houston, Tex.

[22] Filed: Oct. 8, 1975

[21] Appl. No.: 620,668

Related U.S. Application Data

[62] Division of Ser. No. 421,197, Dec. 3, 1973, Pat. No. 3,971,434.

[52] U.S. Cl. ............................ 324/.5 R; 324/.5 AC
[51] Int. Cl.$^2$ ....................................... G01R 33/08
[58] Field of Search .............. 324/.5 R, .5 A, .5 AC

[56] References Cited
UNITED STATES PATENTS

| | | | |
|---|---|---|---|
| 2,864,995 | 12/1958 | Shoolery | 324/.5 R |
| 3,153,756 | 10/1964 | Williams et al. | 324/.5 R |
| 3,740,641 | 6/1973 | Hwang et al. | 324/.5 R |

*Primary Examiner*—Robert Segal
*Assistant Examiner*—Michael J. Tokar
*Attorney, Agent, or Firm*—Ronald R. Reper

[57] ABSTRACT

An apparatus for rapidly conditioning wax samples and a method for determining the oil content of said samples with a nuclear magnetic resonance analyzer are described. A molten wax sample is collected in a sample holder. The holder is then placed in a temperature equilibration chamber where the molten wax is rapidly cooled at a temperature of about 25-33°F with a cold gas stream from a vortex tube. The sample is then heated to a pre-selected equilibration temperature for a preset time at which point the sample is removed from the equilibration chamber. The sample is placed in the analyzer where the nuclear magnetic resonance value of the sample is determined. The sample is removed from the analyzer and weighed. Finally the oil content of the wax sample is obtained from a previously developed correlation between the oil content and the nuclear magnetic resonance value of various wax samples.

3 Claims, 1 Drawing Figure

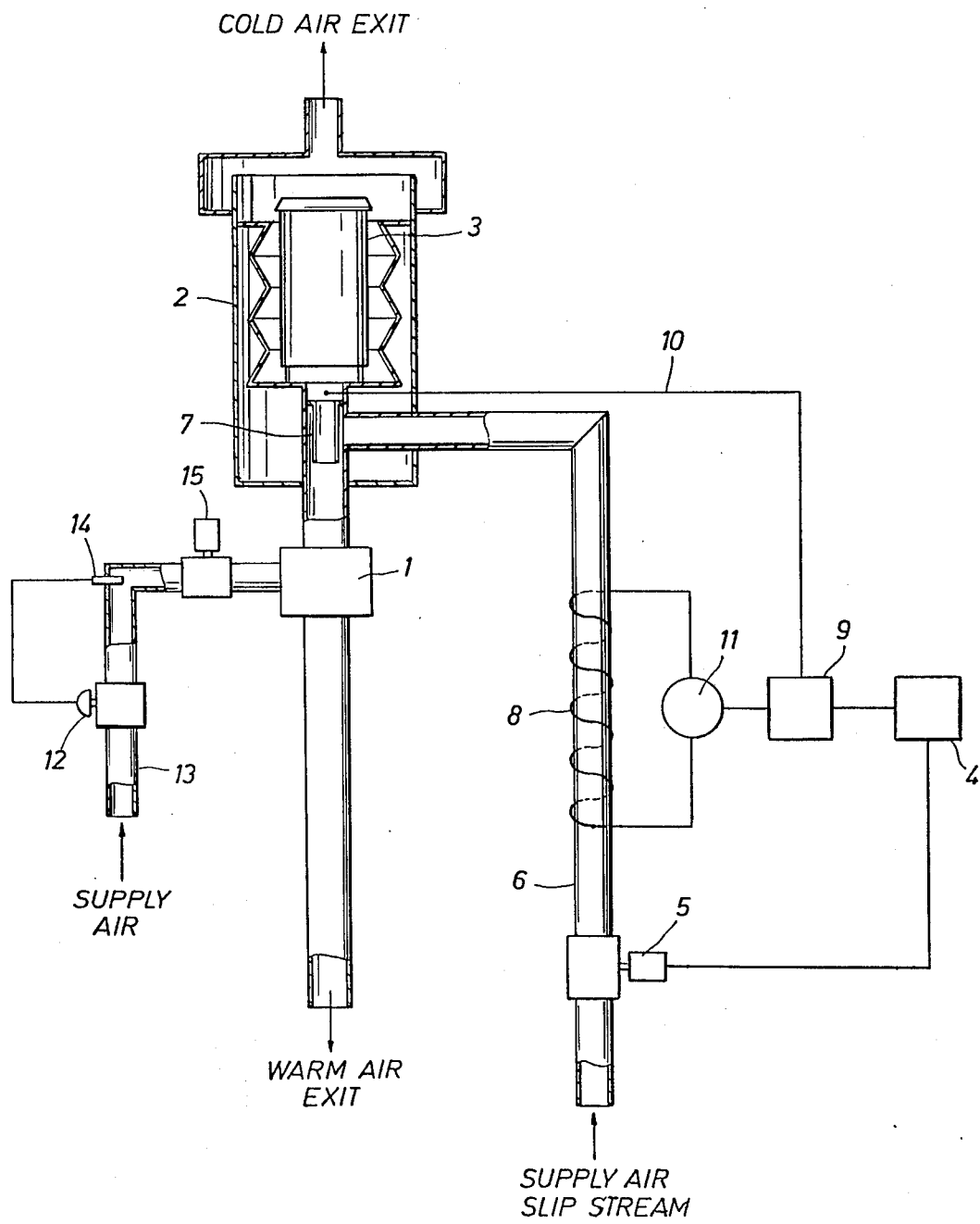

NUCLEAR MAGNETIC RESONANCE TEMPERATURE EQUILIBRATION AND METHOD FOR OIL IN WAX DETERMINATION

This is a division of application Ser. No. 421,197, filed Dec. 3, 1973, now U.S. Pat. No. 3,971,434.

BACKGROUND

The invention relates to an apparatus and a method for determining the oil content of wax samples. In particular it relates to an apparatus and method for rapidly conditioning a wax sample and the determination of its nuclear magnetic reasonance (NMR) value, which is correlated with the oil content of the wax sample.

The oil-in-wax determination is a very important analytical tool in the operation and control of a wax manufacturing unit. Traditionally, the oil content of wax samples has been determined by sending samples from the unit to a laboratory for analysis by ASTM Method D-721 (See Annual Book of ASTM Standards, Part 18, page 129, Nov., 1970). Moreover, effective operation of a commercial deoiling unit is largely dependent upon the determination of oil content in the raw wax stream.

Determination of the oil content of the ASTM method requires that the wax sample be dissolved in methyl ethyl ketone (MEK), then cooled to $-32°$ C to precipitate the wax, followed by filtering. The oil content of the filtrate is then determined by evaporating the MEK and weighing the residue. The accuracy of the determination is reported to be $\pm 0.1\%$ w, but experience has shown that values obtained in routine testing can vary by more than twice that much.

The ASTM test requires a minimum of 1 man hour per test, but the delivery of a sample to the laboratory, scheduling, testing, and reporting of results back to the operating unit, generally results in a time lapse of about 4 hours. The limited reliability of the test frequently results in a reluctance of the unit operator to bypass good wax storage with apparently off-specification wax, or to go back to good wax storage with wax apparently passing specification, unless the analytical results are clear cut, without a second confirming analysis. Thus, a full 8-hour shift can pass before the final disposition of the product wax stream is made. This uncertainty can require reprocessing a large quantity of good wax product, or cause the contamination of a good wax storage tank by failure to divert the stream during plant upsets. Thus, there is considerable economic incentive for the development of a more rapid and reliable means of determining the oil content of product wax streams.

Recently, a relatively inexpensive, broad-line, nuclear magnetic resonance (NMR) instrument called a "Quantity Analyzer," which measures liquids in solids has become commercially available. The adaptation of this equipment to the rapid and reliable determination of the oil content of refinery wax streams is the object of the invention.

THE INVENTION

An apparatus and a routine method for rapidly determining oil-in-wax have now been developed. The method utilizes a commercially available nuclear magnetic resonance analyzer such as the NMR Quantity Analyzer marketed by Newport of North America, Inc. The successful use of this analyzer for the oil-in-wax determination on wax streams depends on a careful and reproducible wax sample conditioning procedure. The apparatus and procedure of this invention permit the use of the NMR value and weight of a wax sample to determine its oil content. A correlation between these values was developed by analyzing various wax samples of known oil content in the NMR.

The NMR measurement of liquids in solids is based upon the fact that the unbound protons, i.e., those present in the liquid components, have a much narrower absorption band width than that due to protons which are essentially immobile in the solid phase. Thus, absorption of energy by the protons in the liquid phase can be selectively detected by the use of appropriate electronic "gating" techniques by which the detector circuit is adjusted to pass only the narrow-band resonance of the liquid, and to exclude the broad-line resonance of the solid.

The Quantity Analyzer is designed around a small permanent magnet of 640 gauss and a radio frequency $(R_f)$ source with a nominal frequency of about 2.7 megahertz. The analyzer contains a port for inserting the solid sample into the magnetic field. Appropriate $R_f$ power is set with a control knob. A tuning control is provided for adjustment of the $R_f$ oscillator to the proton resonance frequency, which is displayed for ease of tuning on an oscilloscope. The proton resonance signal generated by the liquid components of a sample is electronically integrated either as a single determination, or in a repeat mode in which the resonance signal is averaged over one of three standard integration times and repeatedly displayed on a three place digital readout scale. The quantity thus obtained is proportional to the quantity of liquid in the solid sample. Standardization of the analyzer is accomplished by adjustment of an audio frequency (AF) gain control to furnish a preestablished signal level on a standard sample. The remaining controls are generally adjusted initially and do not require further attention. The time required for the actual analysis of a sample is seldom more than two minutes.

To evaluate the NMR for oil-in-wax determinations a set of three wax samples of both Shellwax 200 and Shellmax 500 (microcrystalline) were prepared containing known amounts of oil. The samples were measured as solids by simply cutting them into small pieces and placing them into a glass Nessler tube so that all of the sample could be positioned within the magnetic field. All measurements were made at a probe temperature of $21.4°$ C.

Two sets of measurements were made, first on the solid waxes as received, and then on the same samples after being chilled ($-20°$ F) in a freezer for 2 hours, followed by equilibration overnight at room temperature. The results of the analyses are shown in Table I. The sensitivity was roughly the same, in terms of scale units per percent of oil, for both types of wax, and the NMR response to oil content was linear. Both sets of samples showed a positive NMR readout for zero oil content; however, the signal level for the microcrystalline wax (samples D, E and F) was about four-fold higher than for the paraffin wax (Samples A, B and C). It was quite apparent that the "solid" wax contains protons that exhibit a high degree of mobility, thus accounting for the large signal at zero oil level.

TABLE I

Instrument settings: (Newport Mark II)
R. F. - 500 µA
A. F. Gain - 400
Low-loss setting Integration time - 32 seconds
Supplementary modulation OFF
40 ml sample coil

| SAMPLE* DESIG- NATION | PERCENT OIL | SAMPLE WT., GRAMS | SAMPLES MEASURED AS RECEIVED | | MEASURED AFTER CHILLING AND REWARMING | |
|---|---|---|---|---|---|---|
| | | | NRM READOUT, SCALE UNITS | READOUT PER GRAM | NMR READOUT, SCALE UNITS | READOUT PER GRAM |
| A | 0.1 | 16.45 | 61.3, 61.4 | 3.73 | 56.2, 56.2 | 3.42 |
| B | 0.6 | 17.14 | 65.8, 66.1 | 3.84 | 61.9, 61.9 | 3.61 |
| C | 1.2 | 14.00 | 56.9, 56.8 | 4.06 | 52.3, 52.3 | 3.74 |
| D | Nil to 0.1 | 15.34 | 13.4, 13.3 | 0.870 | 12.7, 12.5 | 0.821 |
| E | 0.3 | 17.37 | 15.9, 15.9 | 0.915 | 16.0, 15.9 | 0.919 |
| F | 0.6 | 18.37 | 18.7, 18.5 | 1.012 | 18.0, 17.8 | 0.975 |
| 20% Newport Standard | — | — | 76.5, 76.7, 76.7 | — | — | — |

*Samples A,B & C are Shellwax-200
Samples D,E & F are Shellmax-500

The effect of temperature treatment suggested that the samples were not completely in phase equilibrium as received. This is not surprising, as waxes have a tendency to supercool and approach phase equilibrium very slowly.

The ability of the analyzer to repeat measurements was tested by measuring the signal of standard samples provided by the instrument manufacturer. These standards for establishing response levels of the analyzer were prepared from slices of ordinary laboratory, black-rubber stoppers enclosed in glass Nessler tubes and immobilized with tight fitting Teflon plugs. These standards provide a strong and unchanging proton resonance signal that can be established to read any desired value by adjustment of the AF gain control. The larger of the two standards was arbitrarily set at 100 and the smaller standard was prepared at one-half that level, or 50. Each standard was measured alternately several times, with ten integrals being taken each time, to note the effect of removing and repositioning samples. The repeatability was excellent.

Since the resonance signal from low concentrations of oil in the wax samples is expected to be small, a standard was prepared in the laboratory to provide a high output signal (190) on the digital readout device (maximum possible reading is 199.9) at an AF gain setting of about 900 (maximum=1000). This standard is 18% relative to the largest standard. These conditions provide maximum sensitivity of the analyzer. Repeatability tests were carried out under these conditions on a practical wax sample (Shellwax 300). Maximum sample quantity was used to further enhance sensitivity.

The wax sample was grated with an ordinary kitchen cheese grater to provide small wax particles that could be tightly packed. These particles were packed to just below the limit line on the sample vial (two inches from the bottom where the magnetic field becomes nonhomogeneous) with a one-inch wooden dowel pin. Repeated integrations were made at each of the preset integration periods available on the instrument. The results are shown in Table II. The readout per gram (RO/GM) of 3.26 is almost three-fold higher at these conditions. The average RO/GM was repeated very closely, and the internal repeatability of each series was markedly improved with an increase in time of integration. Most of the experimental work was carried out using the 18% standard and an integration time of 32 seconds.

TABLE II

| Conditions | |
|---|---|
| $R_f$ | 500µA |
| AF Gain- | 901 |
| 18% STD. Read- | 190 |
| Sample Weight- | 18.18 Grams |

INTEGRATION PERIOD

| 8 Seconds | | 32 Seconds | | 128 Seconds | |
|---|---|---|---|---|---|
| Reading | Δ | Reading | Δ | Reading | Δ |
| 59.0 | 0.0 | 59.7 | −0.5 | 59.0 | +0.3 |
| 58.5 | −0.6 | 59.2 | 0.0 | 58.4 | −0.3 |
| 59.5 | +0.4 | 59.0 | −0.2 | 58.3 | −0.4 |
| 60.8 | +1.7 | 58.9 | −0.3 | 59.0 | +0.3 |
| 58.0 | −1.1 | 59.6 | +0.4 | 58.8 | +0.1 |
| 58.0 | +1.1 | 60.4 | +1.2 | 58.8 | +0.1 |
| 60.4 | +1.3 | 58.3 | −0.9 | 58.1 | −0.6 |
| 60.3 | +1.2 | 58.6 | −0.6 | 58.8 | +0.1 |
| 59.7 | +0.6 | 58.8 | −0.4 | 59.2 | +0.5 |
| 57.1 | −2.0 | 59.4 | +0.2 | 58.5 | −0.2 |
| AVE. 59.1 | ±1.0 | 59.2 | ±0.47 | 58.7 | ±0.29 |

Reading 3.26 UNITS/GRAM

The stability of the $R_f$ power setting during the periods of testing was excellent and the NMR will operate for months with no measurable drift of the power setting from the maximum 500µa. Moreover, no saturation effects were noted at this maximum power setting with any of the wax types.

The effect of temperature was studied on two samples of Shellwax-300 containing differing amounts of oil during a period when the air-conditioning in the laboratory was changing. Both of the was samples and the 18% rubber standard were measured at one hour intervals during the period of changing temperature. There was no significant change in the standard. However, both wax samples showed increasing oil content with rising temperatures, although the temperature change was only 10° F. These results indicate the importance of maintaining a fixed sample temperature for the NMR measurement.

CORRELATION OF NMR AND ASTM METHODS

It is recognized that the ASTM D-721 method for determining oil content will remain the basis for specification testing of finished waxes because of its acceptance by the industry. For this reason, a reliable correlation between the ASTM method and the NMR determined oil content was necessary. Samples had been accumulated for a considerable period of time for this purpose from different types of plant wax runs. All of the NMR measurements were made on samples that had been solidified for at least several days, and the determination of oil content by the ASTM method were single determinations. Correlations were obtained for 141/143, and 158/162 paraffin waxes, and 170/180 microcrystalline wax. All waxes showed a substantial positive NMR signal at "zero oil" content, and the level was substantially different and increased as the melting point of the wax increased. Thus, as expected, separate correlations were required for every wax type.

Successful application of the NMR method to the rapid analysis of product wax streams required a means of conditioning molten wax samples that would be repeatable, rapid, and suitable for use by plant operating personnel. Accordingly, a wax sample conditioning apparatus was developed.

The heart of the "Wax Sample Conditioner" is a vortex tube (obtained from Vortec Corporation, Cinn., Ohio), which provides cold gas for quenching the wax samples. The vortex tube contains no moving parts. A high pressure air stream is fed through nozzles that inject the air tangentially at the circumference of a vortex generation chamber. A vortex is generated and its subsequent behavior is such that hot air is forced out the bottom and cold air exits from the top end of the tube. Differing fractions of hot and cold air can be obtained by changes in inner bushings, and the outlet temperatures of the air streams are also a function of the temperature and pressure of the supply air to the Vortex tube.

The Vortex tube used in this application is a series 200-11L requiring 11 CFM of air flow at 100 psig and 60° F for maximum cooling, although actual conditions used in this application are significantly different. The cold air port (top) of the vortex tube is attached to the base of a thick walled, circular equilibration chamber constructed from Teflon to provide good thermal insulation. The chamber could also be constructed from other suitable insulating materials such as Micarta or Marlex. The chamber is just large enough (2 inches) to allow the gas stream entering the bottom to pass around the wax sample container and out through a small exit port at the top. Spiral vanes have been cut into the walls of the chamber to provide for good gas circulation about the sample vial. A raised cross having the center cut out and standing about ⅛ inch high is milled into the floor of the chamber to allow incoming air from the vortex to pass under and around the sample vial.

The apparatus will now be explained in detail by reference to the drawing.

The vortex tube 1 supplies 25° to 33° F cold gas, to the Teflon equilibration chamber 2 which rapidly chills a molten wax sample inside container 3 for a preselected time, e.g., ten minutes. At the end of the initial cooling cycle, a preset timing relay 4 (Agastat Model 2412AH) actuates a normally closed solenoid valve 5 (ITT General Controls, Inc., Kompact Model K-27 packless valves with SK-502 solenoid) which supplies a slip stream of supply air directly into the equilibration chamber 2 through line 6 where it is mixed with cold air from the vortex tube 1. Mixing of the two gas streams is readily achieved by supplying a baffle 7 which forces the air slip stream to enter the equilibration chamber 2 countercurrently to the flow of cold air. Simultaneously, the timing relay 4 actuates a heater 8 (Briskeat flexible heating tape, ½ inch × 4 ft., 115 v., 192 watts) which heats the slip stream air and permits precise control of the temperature within the equilibration chamber 2.

The baffle 7 is suitably constructed from a copper tubing insert that is flared at the top to seal off the outlet at that point to the hot air. The lower end of the sleeve has grooves cut in the outer surface to give a rotary movement to the incoming hot air which is then well mixed with the cold air from the vortex. Without this baffle, reliable equilibration temperatures could not be achieved.

A temperature controller 9 (API Instruments Co., Model 232) senses the temperature in the equilibration chamber 2, by means of a thermocouple 10, and maintains a preselected temperature (e.g., 75° F) by operating an on-off relay (not shown) which supplies current to the heater on the slip stream air line. A Powerstat Variable Transformer 11 (Model 10B) in the circuit limits the heater current to a desired level. A second time-delay relay (not shown) initiated at the beginning of a sample conditioning run, and preset for 30 minutes, triggers a flashing light that informs the operator that the sample is ready to be measured. Thus, conditioning of the sample is completely automated and requires a total elapsed time of 30 minutes.

Heated air is added to the cold air from the vortex tube to achieve better temperature control than was possible with an on-off operation using the quench air and ambient air. Moreover, it obviates problems expected with large variations in the temperature of plant air.

Efficiency of the vortex tube is affected by the temperature and pressure of the supply air. Supply air is passed through a coil of tubing inside the room to prevent wide swings in air temperature due to changing outside temperatures. An air conditioning expansion valve 12 designed for service with Freon-12 units in the supply air line 13 (with its temperature sensing bulb 14 inside the air line) responds to temperature changes by passing more or less air to the vortex tube 1. This has a stabilizing effect on the temperature of the cold air leaving the vortex. Solenoid valve 15 is actuated by a switch to start the sample conditioning operation. Experiments have shown that the expansion valve is effective in controlling the vortex tube cold gas exit temperature between 25° and 33° F over a range of supply air temperatures from 65° to 90° F.

EXAMPLE

Reliability of the Wax Sample Conditioner was tested with a synthetic blend prepared from raw 141/143 paraffin wax and bright stock oil (0.40%w). This sample was melted and equilibrated overnight at 220° F in a nitrogen atmosphere. Molten wax samples were poured, as needed, into the sample vials. Each sample was conditioned in the Wax Sample Conditioner by the procedure described below followed by measurement on the NMR analyzer. Some changes in the sample handling regimen were intentionally introduced to test the effects of these variations. The results of these experiments are shown in Table III.

TABLE III

| SAMPLE | %w OIL DET'D | Δ | SAMPLE PREPARATION |
|---|---|---|---|
| 1 | 0.42 | +0.03 | STANDARD 30 MINUTES CONDITIONING |
| 2 | 0.43 | +0.04 | " |
| 3 | 0.37 | −0.02 | " |
| 4 | 0.40 | +0.01 | " |
| 5 | 0.37 | −0.02 | " |
| 6 | 0.43 | +0.04 | " |
| 7 | 0.37 | −0.02 | " |
| 8 | 0.37 | −0.02 | ONSET OF CONDITIONING DELAYED 30 MINUTES |
| 9 | 0.36 | −0.03 | " |
| 10 | 0.38 | −0.01 | CONDITIONING EXTENDED 30 MINUTES |
| 11 | 0.40 | +0.01 | RECONDITIONED AFTER OVERNIGHT EQUILIBRATION |
| 12 | 0.40 | +0.01 | QUENCHED AT 33°F* |
| AVE. | 0.39 | ±0.02 | |
| ACTUAL VALUE 0.40%w | | | |

*ALL OTHER SAMPLES WERE QUENCHED AT 27°F

The first seven runs were standard conditioning on replicate samplings. Runs 8 and 9 were each poured into sample vials but were allowed to stand for 30 minutes before conditioning was begun and thus had already solidified somewhat before conditioning. Run 9 was conditioned for 1 hour instead of 30 minutes. These latter runs were intended to simulate delays in the beginning or completing of the conditioning step by busy operators. Run 12 was quenched at a higher temperature (33° F) than all of the other runs (27° F). These results have shown that the automatic Wax Sample Conditioner is very satisfactory for rapidly conditioning molten wax samples. The repeatability is ± 0.02% oil. Some delay in beginning, or terminating, the sample conditioning period can be tolerated, but is not recommended as a routine practice. Small variations in the quench temperature (± 3° F) are not critical.

Wax analyses in the laboratory were obtained using glass Nessler tubes. These tubes are not disposable and pose a serious cleaning problem for routine use in the plant. Accordingly, disposable polystyrene pharmaceutical "pill bottles", available from Sargent-Welch Company, are used in the plant. These inexpensive vials are 23 mm diameter by 52 mm in height and hold about 13 grams of wax. They are equipped with polyethylene caps which can be used during the conditioning step, but must be removed prior to the NMR measurement, as they possess a NMR signal of their own. On the other hand, the background signal from the polystyrene vial is small enough to be ignored.

The NMR signal level is proportional to the quantity of wax in the sample vial, thus the amount of wax must be determined gravimetrically.

Sample Conditioning Procedure

The procedure for conditioning wax samples may be simply stated as follows: the operator collects the samples, using a suitable wax sampler, in a tared plastic vial. (These are usually tared in large quantities and the tare weight is written on the caps with a felt pen). He records the tare weight, places the capped sample vial in the wax sample conditioner, turns on the main switch, and goes about his other duties. In thirty minutes, the sample conditioner signals that the sample is ready for measurement. The operator then places the tuning standard in the NMR probe cavity, and adjusts the tuning with the $R_f$ tuning control (this step requires less than 10 seconds). The tuning standard is withdrawn and replaced with the sample to be analyzed. The integrator button is depressed and, in 32 seconds, the first reading is flashed on the digital readout meter. Usually, three readings are taken and averaged. The operator removes the sample from the probe, discards the vial cap, and weighs the sample. (This step also requires less than 10 seconds). Using the weight of sample and the NMR average reading, the readout per gram (RO/GM) is obtained from printed tables, and the RO/GM in turn gives the oil content from another set of tables. The entire procedure requires less than 5 minutes plus the 30 minutes required for sample conditioning. At the beginning of the day only, the NMR Quantity Analyzer is standardized using the previously mentioned 18% rubber standard to check the standard reading. Although this value (190 ± 0.5) has not changed over an extended period, it requires only a simple adjustment of the AF gain control to re-establish the correct reading on the standard.

What is claimed is:

1. A method for rapidly determining the oil content of wax samples, said method comprising:
   obtaining a molten wax sample in a suitable sample holder;
   placing said sample holder in a suitable temperature equilibration chamber;
   rapidly cooling and solidifying said wax sample at a preselected temperature;
   heating the solid wax sample to a pre-selected equilibration temperature for a preset time suitable for determining the nuclear magnetic resonance value of said sample;
   removing said wax sample from said temperature equilibration chamber after reaching said preselected equilibration temperature in said preset time and placing said sample in a nuclear magnetic resonance analyzer;
   measuring the nuclear magnetic resonance value in said analyzer;
   removing said wax sample from said analyzer and determining the weight of wax; and
   determining the oil content of said wax sample from a previously developed correlation between the weight and oil content of wax samples and the nuclear magnetic resonance values of said wax samples.

2. The method of claim 1 wherein the molten wax sample is solidified by passing a cold gas through said equilibration chamber.

3. The method of claim 1 wherein the molten wax sample to be analyzed is solidified in said temperature equilibration chamber at a pre-selected cooling temperature from 25° to 33° F in about 10 minutes by a cold gas obtained from a vortex tube and said sample is then heated to a pre-selected temperature of about 75° F in about 20 minutes by a heated gas stream.

* * * * *